United States Patent [19]

Lo et al.

[11] Patent Number: 5,310,928
[45] Date of Patent: May 10, 1994

[54] PROCESS FOR PREPARING BIPHENYLTETRAZOLE COMPOUNDS

[75] Inventors: Young S. Lo, Hockessin; Lucius T. Rossano, Newark, both of Del.; Robert D. Larsen, Bridgewater; Anthony O. King, Hillsborough, both of N.J.

[73] Assignees: E. I. Du Pont de Nemours and Company, Wilmington, Del.; Merck & Co., Inc., Rahway, N.J.

[21] Appl. No.: 911,812

[22] Filed: Jul. 10, 1992

Related U.S. Application Data

[63] Continuation-in-part of Ser. No. 793,514, Nov. 18, 1991, Pat. No. 5,130,439.

[51] Int. Cl.$^5$ .................. C07D 257/04; C07D 257/06; C07D 403/06
[52] U.S. Cl. ................... 548/252; 548/250; 548/254
[58] Field of Search ................. 548/250, 252, 254

[56] References Cited

U.S. PATENT DOCUMENTS

| | | | |
|---|---|---|---|
| 4,820,843 | 11/1987 | Aldrich et al. | 548/252 |
| 5,164,518 | 11/1992 | Lavock | 549/79 |

FOREIGN PATENT DOCUMENTS

| | | |
|---|---|---|
| 0291969 | 11/1988 | European Pat. Off. . |
| 0470794 | 2/1992 | European Pat. Off. . |
| 0470795 | 2/1992 | European Pat. Off. . |
| 2100576 | 3/1972 | France . |

OTHER PUBLICATIONS

Bringmann et al., "The Directed Synthesis of Biaryl Compounds: Modern Concepts and Strategies", Angew. Chem. Int. Ed. Engl., vol. 29, 1990, pp. 977-991.

Duncia et al., "Three Synthetic Routes to a Sterically Hindered Tetrazole. A New One-Step Mild Conversion of an Amide into a Tetrazole", J. Org. Chem., 1991, 56, pp. 2395-2400.

Accounts of Chemical Research, vol. 15, No. 10, Oct. 1982, pp. 306-312, Washington, U.S., by P. Beak.

*Primary Examiner*—David B. Springer

[57] ABSTRACT

Method for the preparing biphenyltetrazole compounds which are angiotensin II receptor antagonists or which are useful intermediates to prepare angiotensin II receptor antagonists. An illustrative biphenyl tetrazole compound is 2-n-butyl-4-chloro-1-[(2'-(tetrazol-5-yl)-1,1'-biphenyl-4-yl)methyl]-1H-imidazole-5-methanol, potassium salt.

29 Claims, No Drawings

PROCESS FOR PREPARING BIPHENYLTETRAZOLE COMPOUNDS

CROSS REFERENCE TO RELATED APPLICATIONS

This application is a continuation in part of U.S. application Ser. No. 07/793,514, filed Nov. 18, 1991, now U.S. Pat. No. 130,439.

BACKGROUND OF THE INVENTION

Field of the Invention

This invention is concerned with novel tetrazolylphenylboronic acids and their derivatives, methods for their preparation and their use in processes for the preparation of angiotensin II receptor antagonists which are effective agents for the treatment of hypertension and congestive heart failure.

Background and Prior Art

The successful development of orally active angiotensin converting enzyme (ACE) inhibitors, e.g., captopril, enalapril, etc., for the treatment of hypertension and congestive heart failure has generated great interest in designing new pharmacological blockers of the renin-angiotensin system (RAS). As angiotensin II (AII) is the primary effector molecule of the RAS (Peach, J. J., Renin-Angiotensin System:Biochemistry and Mechanism of Action, Physiol. Rev., 1977, 57:313-370), a receptor antagonist of AII would provide a direct approach to block the system. A number of peptide analogs of AII have been reported to have AII receptor antagonist properties; however, they also retain partial agonist properties and lack oral activities (Corvol, P., New Therapeutic Prospects of Renin-Angiotensin System Inhibition, Clin. Exp. Hypertens.-Theory & Practice, 1989, AII (Suppl. 2), 463-470). More recently, following the disclosure of a few nonpeptide AII antagonist leads (U.S. Pat. No. 4,355,040), several series of AII antagonists have been synthesized at E. I. du Pont de Nemours and Company. Many of these compounds are orally active with potent activities (Wong, P. C., et al., Functional Studies of Nonpeptide Angiotensin II Receptor Subtype-Specific Ligands:DuP753 (AII-1) and DP123177 (AII-2), J. Pharm. and Exp. Ther., 1990, 255 (2), pp 584 to 592 and references therein). These novel compounds were disclosed in European Patent Application 0 324 377 published Jul. 19, 1989.

Many of the AII receptor antagonists have the biphenyl structure as a portion of the molecule. Synthetic methods for the preparations of biphenyls were reviewed recently (Bringmann, G., et al., Angew. Chem. Int. Ed. Engl., 29, 1990, 977 to 991). Also Duncia, et al. (U.S. Pat. No. 4,820,843 and J. Org. Chem., 1991, 56, 2395-2400) described alternate preparations of biphenyls. The preparation, properties, and uses of boronic acids and derivatives were summarized in Metal-Organic Compounds, Advances in Chemistry Series, #23, American Chemical Society, 1959. The ortho-lithiation of 2-substituted 5-phenyl-tetrazoles was disclosed in U.S Pat. No. 5,039,814.

SUMMARY OF THE INVENTION

The novel tetrazolylphenylboronic acid derivatives prepared in accordance with this invention are represented by formula I below

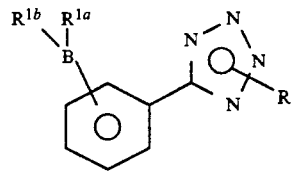

wherein:

P is triphenylmethyl, tertiary-butyl, $C_1$-$C_4$ alkoxymethyl, methylthiomethyl, phenyl $C_1$-$C_4$ alkoxymethyl, p-methoxybenzyl, 2,4,6-trimethylbenzyl, 2-(trimethylsilyl)ethyl, tetrahydropyranyl, piperonyl, or benzenesulfonyl; and $R^{1a}$ and $R^{1b}$ are each independently chlorine, bromine, $C_1$-$C_4$ alkoxy or hydroxy; and $R^{1a}$ and $R^{1b}$ can be taken together with B to form a

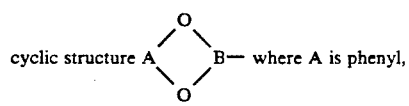

cyclic structure A B— where A is phenyl, or $(CH_2)_n$, where n is 2-4.

The novel compounds of formula I are prepared by reacting a compound represented by the formula

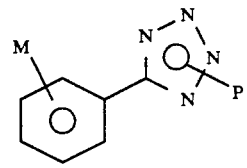

wherein:

P is defined as for formula I above; and

M is a metal selected from the group consisting of lithium, sodium, potassium, or magnesium with a boron compound having the formula

wherein $R^{1a}$ and $R^{1b}$ are as defined for formula I above and $R^{1c}$ is chlorine, bromine or $C_{1-4}$ alkoxy.

The novel tetrazolylphenylboronic acids or derivatives represented by formula I can be reacted further to provide more advanced intermediates that are precursors for AII receptor antagonists. Thus, the compounds of formula I are employed in a cross-coupling reaction with substituted phenyl compounds represented by the formula

wherein

X is bromine, iodine, methanesulfonyloxy, toluenesulfonyloxy, fluorosulfonyloxy, or trifluoromethanesulfonyloxy; and Q is hydrogen, methyl, $C_1$-$C_4$ alkyl, hydroxymethyl, triorganosilyloxymethyl, hydroxy $C_1$-$C_4$ alkyl, formyl, $C_1$-$C_4$ acyl, $C_1$-$C_4$ alkoxycarbonyl, or W—L— wherein L is a single bond, —$(CH_2)_t$ where t is 1 to 4, —$(CH_2)_rO(CH_2)_r$—, —$(CH_2)_r$-S(O)$_r$— where r is 0 to 2 and W is a mono-, bi-, or multi-cyclic heteroaromatic group, which may be partially or completely hydrogenated, in which each ring member of said group includes at least 1 carbon atom and from 1 to 5 heteroatoms. For purposes of the present invention, preferably W is a group of the following formula:

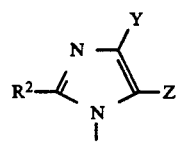

wherein $R^2$ is $C_1$-$C_4$ alkyl, Y is $C_1$-$C_4$ alkyl, $C_1$-$C_4$ perfluoroalkyl, halogen, phenyl unsubstituted or substituted with one or two substituents selected from $C_1$-$C_4$ alkyl, F, Cl, $CF_3$, $C_1$-$C_4$ alkoxyl, phenoxyl, phenyl; phenyl $C_1$-$C_4$ alkyl and Z is hydroxymethyl, formyl, $C_1$-$C_4$ acyl, $C_1$-$C_4$ alkoxylcarbonyl, carboxyl; and where Y and Z can be taken together to form a 5-, 6-, or 7-membered ring containing 1 to 2 heteroatoms selected from nitrogen, sulfur, or oxygen.

The products of this cross-coupling reaction are compounds of the formula

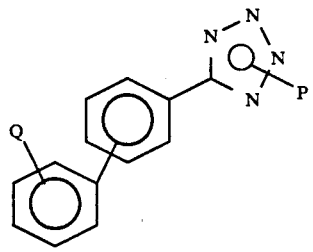

wherein P and Q have the meanings given above and the position of

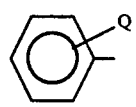

relative to the tetrazole is the same as the position of

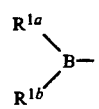

relative to the tetrazole in formula I.

Thus an overall reaction scheme contemplated as a part of this invention can be presented by the following

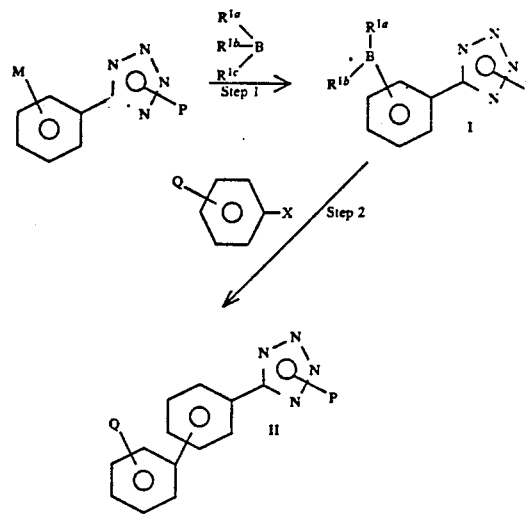

wherein M, X, P, $R^{1a}$, $R^{1b}$, $R^{1c}$ and Q have the meanings given above.

It is therefore an object of the present invention to provide novel and efficient processes for the preparation of novel tetrazolylphenylboronic acids and derivatives, and the preparation of more advanced intermediates of AII receptor antagonists in subsequent reactions.

Additional objects and advantages of the present invention will be apparent to one skilled in the art and still others will become apparent from the following description for carrying out the present invention and the appended claims.

DETAILED DESCRIPTION OF THE INVENTION

In step 1 of the overall reaction scheme shown above the carbanion having the formula

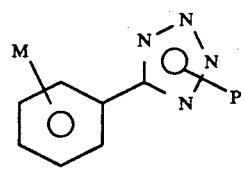

and the boron compound having the formula

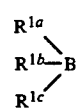

are reacted together.

The meanings given above for P, the protecting group for the tetrazole substituent in formula I are those considered the most preferred for purposes of the invention. However, since tetrazoles are isosteric with carboxyl groups and the protecting group is blocking a nitrogen, many of the protecting groups used for the carboxyl group and the amine group also are useful for the tetrazole group. Therefore, one skilled in the art may refer to the text "Protective Groups in Organic Synthesis" (in particular, Chapters 5 and 7), Theodora W. Green, John Wiley & Sons, 1981, for the selection of other possible protecting groups that could be utilized for purposes of the present invention. Applicants hereby incorporate by reference the disclosure of this text for a more complete definition of the protecting group P.

The reaction is conducted in an aprotic solvent, for example, tetrahydrofuran, diethyl ether, benzene, etc., at a temperature ranging from −70° C. to 25° C., preferably −30° C. to 0° C. Due to the moisture-sensitive nature of the reactants, the reaction is conducted in an inert atmosphere such as nitrogen.

The novel tetrazolylphenylboronic acid ($R^{1a}$ and $R^{1b}$=OH) can be isolated from the reaction mixture by the addition of isopropanol-water or water and maintaining the pH in the range of 3 to 10, with mineral acids such as phosphoric acid, carboxylic acids such as acetic acid, ammonium salts such as ammonium chloride, or carbonic acid salts such as sodium carbonate. The novel tetrazolylphenylboronic acid derivatives ($R^{1a}$ and $R^{1b}$=$C_1$-$C_4$ alkoxy, Cl, Br) can be used in step 2 without isolation.

The novel tetrazolylphenylboronic acid ($R^{1a}$ and $R^{1b}$=OH) can be prepared from 5-phenyltetrazole, which is readily available commercially, in a one-pot procedure as illustrated in Part B of Example 1.

In step 2, a novel compound prepared in step 1 is reacted with an electrophile having the formula

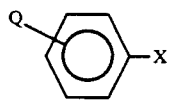

in a solvent in the presence of a metal catalyst and a base for one to thirty hours at a temperature ranging from room temperature to 150° C., preferably 60° C. to 90° C. The coupling solvents for the reaction can be selected from a variety of known process solvents. Illustrative of the coupling solvents that can be utilized either singly or in combinations are benzene, toluene, ethyl ether, tetrahydrofuran, dioxane, acetonitrile, dimethylformamide, dimethylacetamide, ethanol, methanol, propanol, water, 2-methyltetrahydrofuran or diethoxymethane. Preferably in combination with water.

The metal catalyst is a complex of nickel, palladium, or platinum, preferably a palladium complex such as tetrakis(triphenylphosphine)palladium, bis(dibenzylideneacetone)palladium, tris(dibenzylideneacetone)dipalladium, a phosphinated palladium II complex selected from the group consisting of: bis(triphenylphosphine)palladium chloride, bis(triphenylphosphine)palladium bromide, bis(triphenylphosphine)palladium acetate, bis(triisopropylphosphite)palladium chloride, bis(triisopropylphosphite)palladium bromide, bis(triisopropylphosphite)palladium acetate, [1,2-bis(diphenylphosphino)ethane]palladium chloride, [1,2-bis(diphenylphosphino)ethane]palladium bromide, [1,2-bis(diphenylphosphino)ethane]palladium acetate, [1,3-bis(diphenylphosphino)propane]palladium chloride, [1,3-bis(diphenylphosphino)propane]palladium bromide, [1,3-bis(diphenylphosphino)propane]palladium acetate, [1,4-bis(diphenylphosphino)butane]palladium chloride, [1,4-bis(diphenylphosphino)butane]palladium bromide and [1,4-bis(diphenylphosphino)butane]palladium acetate.

The active catalyst may be prepared in advance or generated in the reaction mixture. For example, addition of tris(dibenzylideneacetone)dipalladium to a reaction mixture containing triphenylphosphine in a catalyst forming solvent generates the active triphenylphosphine palladium complex.

The active catalyst can also be prepared from a Pd(II) salt such as palladium chloride, palladium bromide or palladium acetate with triarylphosphine, typically triphenylphosphine under the action of reducing agents such as diakylzinc, alkylzinc halide, dialkylmagnesium, alkylmagnesium halide, trialkylaluminum, dialkylaluminum hydride, sodium borohydride, hydrazine, or arylboronic acid in the presence of a catalyst forming solvent. The preferable reducing agent is diethylzinc.

The catalyst forming solvents for the reaction can be selected from a variety of known process solvents. Illustrative of the catalyst forming solvents that can be utilized either singly or in combinations are benzene, toluene, ethyl ether, tetrahydrofuran, dioxane, acetonitrile, dimethylformamide, dimethylacetamide, dimethylsulfoxide, ethanol, methanol, propanol, water, 2-methyltetrahydrofuran or diethoxymethane. Preferably the catalyst forming solvent is tetrahydrofuran or toluene.

There are a variety of bases that can be used for effecting the reaction. Illustrative examples are organic tertiary non-nucleophilic bases such as triethylamine or diisopropylethylamine, inorganic bases such as potassium carbonate, sodium carbonate, cesium carbonate, thallium carbonate, potassium hydroxide, sodium hydroxide, thallium hydroxide, or the alkoxides of these alkali metals. When an inorganic base insoluble in the organic solvent is used, dissolution in water may be necessary; the use of a phase-transfer catalyst such as tetra-n-butylammonium bromide or crown ether also facilitate the reaction. Organic solvent soluble bases such as tetra-n-butylammonium carbonate or tetra-n-butylammonium hydroxide, benzyltrimethylammonium carbonate, benzyltrimethylammonium methyl carbonate, benzyltrimethylammonium methoxide or benzyltrimethylammonium hydroxide, or other basic tetraalkylammonium compounds are particularly useful in certain cases. The organic solvent soluble base maybe prepared in advance or generated in the reaction mixture. For example, the preparation of benzyltrimethylammonium carbonate in which benzyltrimethylammonium hydroxide solution is reacted with ammonium carbonate.

The purification of the product of Step 2, formula II, maybe aided by the addition of trialkylphosphine in the crystallization of the compound of formula II or by the addition of trialkylphosphine during the recrystallization process. The purification is preferably aided by the presence of tributylphosphine.

Step 2 is such a general reaction that it tolerates a variety of functional groups as illustrated by literature examples (V. Snieckus, Chem. Rev., 1990, 90, 879–933 and references therein). Therefore, when Q has the previously given meaning W—L—, W may be any of various heterocyclic systems, including among others, imidazoles, triazolinones, quinazolinones, imidazolones, pyrazoles, pyrimidinones, or pyrroles. Accordingly, many of the AII receptor antagonists disclosed recently can be synthesized by the process disclosed in this invention. Applicants hereby incorporate by reference the disclosures of the following European Patent Office Applications for a more complete definition of the scope of heterocyclic systems that may be included as W in step 2 of the general reaction of this invention: EP 419048, EP 424317, EP 426021, EP 420237, EP 425921, EP 430300, EP 429257, EP 430709, EP 425211, EP 427463, EP 432737, EP 400974, EP 411766, EP 407342, EP 411507, EP 412848, EP 401030, EP 407102, EP 409332, EP 392317, EP 399731, EP 399732, EP 400835, EP 415886, EP 412594, EP- 403158, EP 403159.

For example, EP 400974 disclosed AII receptor antagonists wherein the portion of the general formula shown below is equivalent to the definition of Q, where Q is W—L, for the present invention:
L is —(CH$_2$)—; and
W is a bicyclic heteroaromatic group having the structure:

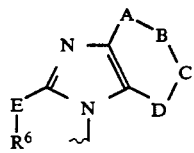

wherein
E is a single bond, —NR$^{13}$(CH$_2$)$_s$—, —S(O)$_x$—(CH$_2$)$_s$— where x is 0 to 2 and s is 0 to 5, —CH(OH)—, —O—, —CO—;
R$^6$ is
(a) phenyl or naphthyl optionally substituted with 1 or 2 substituents selected from the group consisting of halo (Cl, Br, I, F), —O—C$_1$-C$_4$ alkyl, —C$_1$-C$_4$ alkyl, NO$_2$, CF$_3$, —SO$_2$NR$^9$R$^{10}$, —S= C$_1$-C$_4$ alkyl, —OH, NH$_2$, —C$_3$-C$_7$ cycloalkyl, —C$_3$-C$_{10}$-alkenyl;
(b) straight chain or branched C$_1$-C$_9$-alkyl, C$_2$-C$_6$-alkenyl or C$_2$-C$_6$-alkynyl each of which can be optionally substituted with a substituent selected from the group consisting of aryl, where aryl is phenyl or naphthyl optionally substituted with one or two substituents selected from the group consisting of halo(Cl, Br, I, F), C$_1$-C$_4$-alkyl, C$_1$-C$_4$-alkoxy, NO$_2$, CF$_3$, C$_1$-C$_4$-alkylthio, OH, NH$_2$, NH(C$_1$-C$_4$-alkyl), N(C$_1$-C$_4$-alkyl)$_2$, CO$_2$H, and CO$_2$-C$_1$-$_{C4}$-alkyl; C$_3$-C$_7$-cycloalkyl; halo(Cl, Br, I, F); —OH; —NH$_2$; —NH(C$_1$-C$_4$-alkyl); —CF$_2$CF$_3$; —N(C$_1$-C$_4$-alkyl)$_2$; —NH—SO$_2$R$^4$; —COOR$^4$; —CF$_3$; —CF$_2$CH$_3$; —SO$_2$NHR$^9$; or
(c) an unsubstituted, monosubstituted or disubstituted aromatic 5 or 6 membered cyclic ring which can contain one or two members selected from the group consisting of N, O, S, and wherein the substitutents are members selected from the group consisting of —OH, —SH, C$_1$-C$_4$-alkyl, C$_1$-C$_4$-alkyloxy CF$_3$, Halo(Cl, Br, I, F), or NO$_2$,
(d) perfluoro-C$_1$-C$_4$-alkyl,
(e) C$_3$-C$_7$-cycloalkyl optionally mono- or disubstituted with C$_1$-C$_4$-alkyl or CF$_3$;
R$^4$ is straight chain or branched C$_1$-C$_6$-alkyl, aryl or —CH$_2$-aryl where aryl is as defined above;
R$^9$ is H, C$_1$-C$_5$-alkyl, aryl or —CH$_2$-aryl where aryl is as defined above;
R$^{10}$ is H, C$_1$-C$_4$-alkyl;
R$^{13}$ is H, —CO(C$_1$-C$_4$-alkyl), C$_1$-C$_6$-alkyl, allyl, C$_3$-C$_6$-cycloalkyl, phenyl or benzyl;
—A—B—C—D— represents the constituent atoms of a 6-member unsaturated heterocyclic ring with the imidazole to which they are attached containing 1 to 3 nitrogen atoms and includes the following:

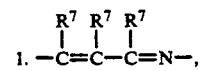
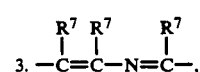
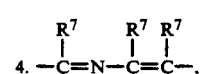
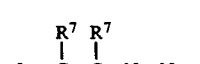
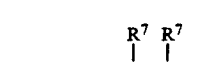
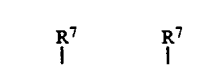
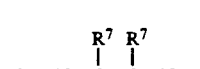
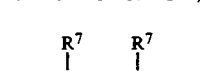
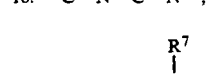
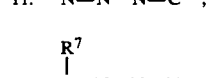
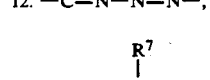
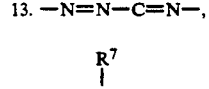
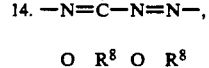
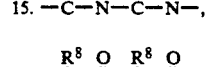
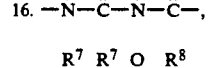
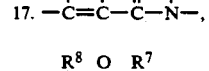

-continued

19. 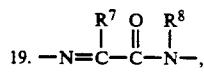

20. 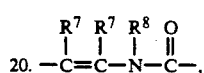

21. 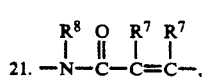

22. 

23. 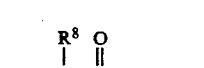

24. 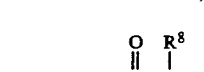

25. 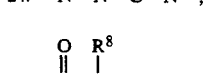

26. 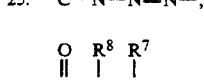

27. 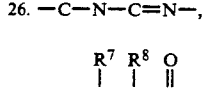

28. 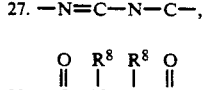

29. 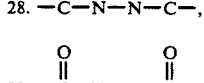

30. 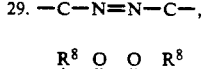

31. 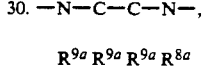

32. 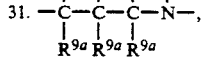

33. 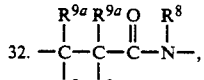

34. 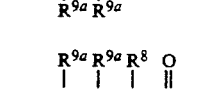

35. 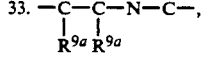

36. 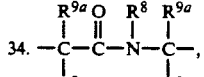

-continued

37. 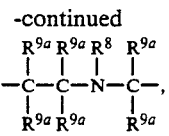

wherein:

$R^7$ groups can be the same or different and represent:
a) hydrogen,
b) $C_1$-$C_6$ straight or branched chain alkyl, or $C_2$-$C_6$ alkenyl, or alkynyl each of which is unsubstituted or substituted with:
  i) —OH,
  ii) —$C_1$-$C_4$-alkoxy,
  iii) —$CO_2R^4$,
  iv) —$COR^4$,

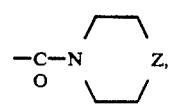 v)

vi) —$CON(R^4)_2$,

 vii)

viii) —$N(R^4)$hd,
ix) —aryl as defined above,
x) —heterocyclic as defined in (O) below,
xi) —$S(O)_xR^{23}$,
xii) —tetrazol-5-yl,
xiii) —$CONHSO_2R^{23}$,
Xiv) —$SO_2NH$-heteroaryl,
xv) —$SO_2NHCOR^{23}$,

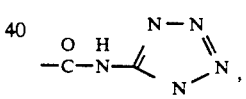 xvi)

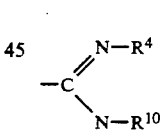 xvii)

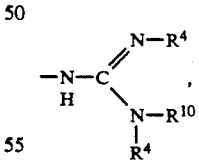 xviii)

xix) —$PO(OR^4)_2$,
xx) —$PO(OR^4R^9)$,
c) halo, such as chloro, bromo or iodo,
d) perfluoro-$C_1$-$C_4$-alkyl,
e) —OH,
f) —$NH_2$,

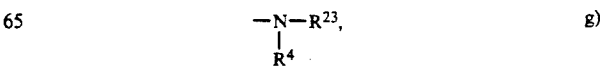 g)

-continued

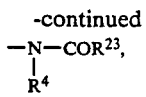  h)

i) —OR$^{23}$,
j) —CO$_2$R$^4$,
k) —CON(R$^4$)$_2$,
l) —NH—C$_3$-C$_7$-cycloalkyl,
m) —C$_3$-C$_7$-cycloalkyl,
n) aryl as defined above, or
o) heterocyclic which is a five- or six-membered saturated or unsaturated ring containing up to three heteroatoms selected from the group consisting of O, N or S wherein S may be in the form of sulfoxide or sulfone and which may be optionally substituted with one or two substituents which are members selected from the group consisting of halo (Cl, Br, F, I), C$_1$-C$_4$-alkyl, C$_1$-C$_4$-alkoxy, C$_1$-C$_4$S(O)$_x$— where x is as defined above, CF$_3$, NO$_2$, OH, CO$_2$H, CO$_2$-C$_1$-C$_4$-alkyl, NH$_2$, NH(C$_1$-C$_4$-alkyl) or N(R$^4$)$_2$;
p) —CN,

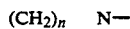

where n is 4 to 6,
r) —SO$_2$N(R$^4$)$_2$,
s) —tetrazol-5-yl,
t) —CONHSO$_2$R$^{23}$,
u) —PO(OR$^4$)$_2$,
v) —NHSO$_2$CF$_3$,
w) —SO$_2$NH-heteroaryl,
x) —SO$_2$NHCOR$^{23}$,
y) —S(O)$_x$R$^{23}$,

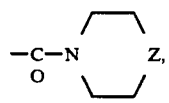

aa) —PO(OR$^4$)R$^9$,
bb) —NHSO$_2$R$^{23}$,
cc) —NHSO$_{2NH}$R$^{23}$,
dd) —NHSO$_{2NHCO}$R$^{23}$,
ee) —NHCONHSO$_2$R$^{23}$,

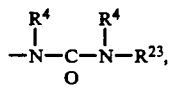

hh) —CO-aryl,

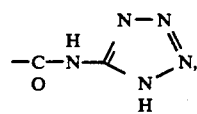  ii)

jj) —CO—C$_1$-C$_4$-alkyl,
kk) —SO$_2$NH—CN,

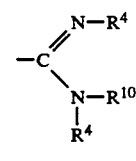  ll)

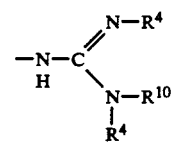  mm)

R$^8$ groups can be the same or different and represent:
a) hydrogen
b) C$_1$-C$_5$-alkyl or alkenyl either substituted or unsubstituted with hydroxy, C$_1$-C$_4$-alkoxy, —N(R$^4$)$_2$, —COR$^4$ or C$_3$-C$_5$-cycloalkyl,
c) C$_3$-C$_5$-cycloalkyl, R$^{8a}$ is R$^8$ or C$_1$-C$_4$-acyl;

R$^{9a}$ groups can be the same or different and represent:
a) hydrogen,
b) C$_1$-C$_5$-alkyl or alkenyl either substituted of unsubstituted with
i) hydroxy,
ii) —CO$_2$R$^4$,
iii) —CONHR$^4$, or
iv) —CON(R$^4$)$_2$;

R$^{23}$ is (a) aryl as defined above,
(b) heteroaryl, wherein heteroaryl is an unsubstituted, monosubstituted or disubstituted five- or six-membered aromatic ring which can optionally contain 1 to 3 heteroatoms selected from the group consisting of O, N, or S and wherein the substitutents are members selected from the group consisting o —OH, —SH, —C$_1$-C$_4$- alkyl, —C$_1$-C$_4$-alkoxy, halo(Cl, Br, F, I), —NO$_2$, —CO$_2$H, —CO$_2$—C$_1$-C$_4$-alkyl, —NH$_2$, —NH(-C$_1$-C$_4$-alkyl) and —N(C$_1$-C$_4$-alkyl)$_2$,
(c) C$_3$-C$_4$-cycloalkyl,
(d) C$_1$-C$_4$-alkyl which can be optionally substituted with a substituent that is a member selected from the group consisting of aryl as defined above, heteroaryl as defined above, —OH, —SH, —C$_1$-C$_4$-alkyl, —O(C$_1$-C$_4$-alkyl), —S(-C$_1$-C$_4$-alkyl), —CF$_3$, Halo(CL, BR, I, F), NO$_2$, —CO$_2$H, —CO$_2$—C$_1$-C$_4$-alkyl, —NH$_2$, —NH(-C$_1$-C$_4$-alkyl), —NHCOR$^{4a}$, —N(C$_1$-C$_4$-alkyl)$_2$, PO$_3$H, —PO(OH)(C$_1$-C$_4$-alkyl), —PO(OH)(aryl) or —PO(OH)(O—C$_1$-C$_4$-alkyl),
(e) perfluoro-C$_1$-C$_4$-alkyl;

R$^{4a}$ is C$_1$-C$_6$-alkyl, aryl or —CH$_2$-aryl where aryl is as defined above;

gg) or the pharmaceutically acceptable salt thereof.

Preferred bicyclic heteroaromatic groups of the aforesaid structure disclosed in EP400974 are where:
E is a single bond;
R$^6$ is —C$_2$-alkyl; and
—A—B—C—D— represents the constituent atoms of a 6-member unsaturated heterocyclic ring with the imidazole to which they are attached containing 1 to 3 nitrogen atoms and includes the following:

-continued $$-\overset{R^7}{\underset{|}{C}}=\overset{R^7}{\underset{|}{C}}-N=N-,$$

$$-N=\overset{R^7}{\underset{|}{C}}-\overset{R^7}{\underset{|}{C}}=N-,$$

$$-\overset{R^7}{\underset{|}{C}}=N-\overset{R^7}{\underset{|}{C}}=N-,$$

$$-\overset{R^8}{\underset{|}{N}}-\overset{O}{\underset{\|}{C}}-\overset{R^8}{\underset{|}{N}}-\overset{O}{\underset{\|}{C}}-,$$

$$-\overset{O}{\underset{\|}{C}}-\overset{R^8}{\underset{|}{N}}-\overset{R^8}{\underset{|}{N}}-\overset{O}{\underset{\|}{C}}-,$$

$$-\overset{O}{\underset{\|}{C}}-\overset{R^8}{\underset{|}{N}}-N=N-.$$

As another example, EP 399731 discloses AII receptor antagonists wherein the portion of the general formula shown below is equivalent to the definition of Q, where Q is W—L, for the present invention:

L is —(CH$_2$)—; and

W is a bicyclic heteroaromatic group having the structure:

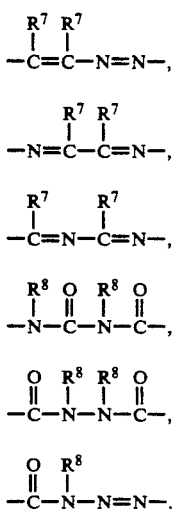

wherein

A, together with the adjacent vinylene group of the imidazole moiety completes an azene ring selected from pyridine, pyrimidine, pyridazine or pyrazine ring;

R$^{1'}$ is (1-8C)alkyl, (3-8C)cycloalkyl, (3-8C)cycloalkyl-(1-4C)alkyl, phenyl or phenyl(1-4C)alkyl;

R$^{2'}$ is hydrogen, (1-4C)alkyl, (1-4C)alkoxy, halo(Cl, Br, F, I) trifluoromethyl, cyano or nitro;

R$^{3'}$ and R$^{4'}$ are optional substituents on the said azene ring, independently selected from hydrogen, (1-4C)alkyl, (3-8C) cycloalkyl, (1-4C)alkoxy, halo(Cl, Br, F, I) trifluoromethyl, cyano, hydroxy, hydroxymethyl, formyl, and nitro; or when A together with the imidazole moiety to which it is attached is an imidazo[4,5-b]pyridine or imidazo[4,5-c]pyridine group, R$^{3'}$ and R$^{4'}$ when they are on adjacent carbon atoms of A form a trimethylene or tetramethylene group, or together with the adjacent vinylene group of A complete a benzene ring, the later optionally bearing a halo(Cl, Br, I, F), (1-4C)alkyl or (1-4C)alkoxy substituent; or A together with the imidazole moiety to which it is attached is other than 1H-imidazo[4,5-c]pyridine ring, one of R$^{3'}$ or R$^{4'}$ is a carboxy or (1-6C)alkoxycarbonyl group and the other is as defined above, or the pharmaceutically acceptable salt thereof.

It will be appreciated that the following ten different groups of imidazopyridines (formulae Ia-Id) and imidazodiazines (formulae Ie-Ij) are encompassed within the above definition of W:

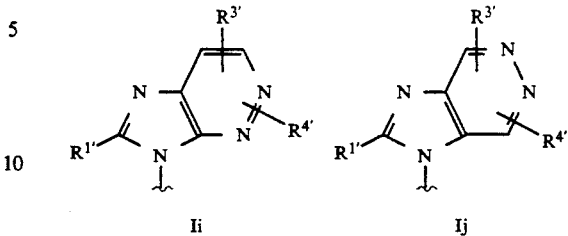

Ii   Ij

The invention is more fully exemplified and taught by the following examples.

EXAMPLE 1

2-(2'-Triphenylmethyl-2'H-tetrazol-5'-yl)phenylboronic acid

Part A

To a 22L flask under nitrogen purge was charged 8.25L acetone, followed by 1.1 kg 5-phenyltetrazole. Triethylamine (800 g) was added in such a rate that the temperature was maintained below 35° C. with some cooling. Solid trityl chloride was charged to this light suspension in five 440 g portions. The temperature was maintained below 35° C. An additional 1.38L acetone was added to the reaction which was then maintained at 25° to 30° C. with stirring for 2 hours. Water (2.2L) was added and the mixture was chilled to 15° to 20° C. The solid was collected by filtration; the filter cake was rinsed with 1.65L 50% acetone-water followed by excess amount of water. The wet cake was re-slurried in 8L acetone and 8L of water was added slowly. The suspension was stirred for 1 hour then filtered. The filter cake was rinsed with 3 to 5L of water. The white solid was dried in a vacuum oven at 40°–45° C. to a constant weight of 3.0 kg, mp 158°–160° C.

To a dry 12L flask under nitrogen purge was charged 3.19L of dry tetrahydrofuran (THF). With agitation, 398 g of 5-phenyl-2-trityl-tetrazole prepared above was charged. The system was evacuated and released to nitrogen three times and then cooled to −20° C. A solution of butyl lithium in heptane (1.6M, 477 g) was then added to the reaction mixture while maintaining the temperature at −15° C. to −20° C. The resultant deep red solution was stirred at −5° C. for 1 hour during which time the lithium salt crystallized out. The solid suspension was cooled to −25° C. again and 333 g triisopropylborate was charged at a temperature range of −20° to −25° C. After the addition, the mixture was allowed to warm to 20° C. without heating. About 2.5L of solvent was removed by vacuum distillation. The pot temperature was kept below 40° C. To the mixture was then added 2.66L of 3% acetic acid in water and the resultant suspension was stirred for 1 hour. The white solid was collected by filtration. The solid cake was rinsed with 1.5L of 20% tetrahydrofuran in water, followed by 3L of water. The solid was dried under vacuum at room temperature to a constant weight of 502.3 g, mp 142°–146° C. (dec.).

Part B

A preferred alternative procedure for preparing the title compound of this Example 1 is by means of the following procedure.

5-Phenyltetrazole (14.6 g, 100 mmol) was suspended in dry THF (120 ml) under nitrogen and triethylamine (14.8 ml, 105 mmol) was added while maintaining the temperature at 15° to 20° C. Triphenylchloromethane (29.3 g, 105 mmol) in dry THF (60 ml) was then added slowly to the mixture at ≦25° C. After the addition was complete the mixture was warmed to 35° C. for 1 hour and then cooled at 0° C. for 1 hour. The precipitated triethylammonium chloride was filtered and the filtrate was degassed via vacuum/nitrogen purges (3×). The degassed solution was cooled to −20° C. and butyllithium (1.6M in hexanes) was added until a pink color persisted for 2 minutes. The pink color indicated that the solution was completely dry. More butyllithium (65.6 ml, 105 mmol) was charged at ≦−15° C. The deep red heterogeneous mixture was aged at −20° to −15° C. for 1 hour and triisopropylborate (30.6 ml, 130 mmol) was added while maintaining the temperature at ≦−15° C.

The deep red solution was aged at −15° C. for 30 minutes and then warmed to 10° C. over 1 hour. The mixture volume was reduced by ~200 ml in vacuo at ≦15° C. at which time <5% of hexanes (vs THF) remained. The residue was diluted with THF to a total volume of 160 ml and isopropanol (60 ml) was added. The solution was cooled to 0° C. and saturated aqueous ammonium chloride (40 ml, 200 mmol) was charged within 15 minutes. The mixture was aged at 20° to 25° C. for 30 minutes and water (100 ml) was added over 30 to 45 minutes. After aging the mixture for 1 hour, the crystallized product was collected by filtration and washed with cold 80% aqueous isopropanol. The filter cake was air dried on the filter to give 69.7 g (86% yield, corrected for 82% purity) of product as the THF mono-solvate.

EXAMPLE 2

3-(2'-Triphenylmethyl-2'H-tetrazol-5'-yl)phenylboronic acid m-Bromobenzonitrile (0.102 m) was dissolved in 130 mL of toluene and the solution was heated to boiling and 30 mL of solvent was distilled under nitrogen purge. After cooling down to room temperature, tri-n-butyl tin chloride (0.102 m) and sodium azide (0.1 m) were charged to the reaction and the mixture was heated at reflux for 18 hours. To the cooled down mixture was added 60 mL toluene and a solution of sodium hydroxide (0.12 m) in 12 mL water. After stirring at room temperature for 5 minutes, triphenylmethyl chloride (0.08 m) was added as a solid and the mixture was stirred for 1 hour. Another charge of triphenylmethyl chloride (0.02 m) was then made and the agitation continued for another hour. The reaction was worked up by addition of 50 mL water, basified with a small amount of sodium hydroxide. The layers were separated and the organic layer was extracted once with 50 mL water, followed by 50 mL saturated sodium chloride solution. The organic layer was dried over anhydrous sodium sulfate, filtered through Celite and the filtrate was concentrated on a rotary evaporator. The residual oil was triturated with 200 mL of n-heptane and chilled in an ice bath. The solid was collected by filtration and rinsed with cold n-heptane. The filter cake was dried in a vacuum oven at 40° to 50° C. until constant weight.

The 2-triphenylmethyl-5-(m-bromophenyl)-2H-tetrazole obtained as described above is treated with n-butyllithium in tetrahydrofuran to generate the lithium salt of the carbanion, 2-triphenylmethyl-5-(m-lithiophenyl)-2H-tetrazole, which in turn is reacted with triisopropylborate to produce the title compound according to the procedure of Part A of Example 1.

EXAMPLE 3

4-(2'-Triphenylmethyl-2H-tetrazol-5'-yl)phenylboronic acid

Starting with p-bromobenzonitrile and using the procedure of Example 2, the title compound is prepared.

EXAMPLE 4

5-(4'-Methyl-1,1'-biphenyl-2-yl)-2-triphenylmethyl-2H-tetrazole 2-(2'-Triphenylmethyl-2'H-tetrazol-5'-yl)phenylboronic acid (Example 1, 0.02 m=9 g), p-bromotoluene (0.022 m=3.84 g), sodium carbonate (0.04 m=4.24 g), toluene (70 mL), and water (20 mL) were charged to a reaction flask. The system was evacuated and released to nitrogen three times and then maintained under a nitrogen atmosphere. Tetrakistriphenylphosphine palladium (0.6 mm=0.693 g) was charged to the reaction mixture which was then heated at 80° C. for 10 hours. The reaction was cooled to room temperature. The organic layer was separated and extracted with 50 mL of water. The organic layer was dried over anhydrous sodium sulfate and concentrated. The residue was crystallized from toluene-n-heptane to give 6.76 g (71% yield) of title compound, mp 164°–166° C. (dec.).

EXAMPLE 5

5-(4'-Bromomethyl-1,1'-biphenyl-2-yl)-2-triphenylmethyl-2H-tetrazole

A mixture of 5-(4'-methyl-1,1'-biphenyl-2-yl)-2-triphenyl-2H-tetrazole (0.195 m=93.5 g), N-bromosuccinimide (0.215 m=38.2 g), VAZO®52 (2.37 g), and 563 g of methylene chloride was stirred and refluxed for 7 hours. The reaction mixture was cooled to room temperature and washed once with 375 mL of water, followed by a solution of 18.8 g of sodium bicarbonate in 357 mL of water. The methylene chloride solution was concentrated and the residue was triturated with 591 g of heptanes. The slurry was chilled to 0° C. before filtration. The solution was rinsed with 1:6 methylene chloride/heptanes and then dried in a vacuum oven at 50° C. to give 102.7 g of title compound.

EXAMPLE 6

2-n-Butyl-4-chloro-1-[(2'-(2-triphenylmethyl-2H-tetrazol-5-yl)-1,1'-biphenyl-4-yl)methyl]-1H-imidazole-5-carboxaldehyde A mixture of 5-(4'-bromomethyl-1,1'-biphenyl-2-yl)-2-triphenylmethyl-2H-tetrazole (0.102 m=63.1 g), 2-n-butyl-4-chloro-1H-imidazole-5-carboxaldehyde (0.113 m=21.1 g) and anhydrous potassium carbonate (0.135 m=18.6 g) in 251 g of N,N-dimethylacetamide was stirred at 0°–5° C. for 8 hours and the temperature of the reaction was raised to 25° C. for an additional 4 hours. Normally the product of this step was not isolated but reduced with sodium borohydride to give 2-n-butyl-4-chloro-1-[(2'-(2-triphenylmethyl-2H-tetrazol-5-yl)-1,1'-biphenyl-4-yl)methyl]-1H-imidazole-5-methanol. The title compound can be isolated by extraction into toluene from aqueous N,N-dimethylacetamide, concentration of the toluene solution, and crystallization from ethyl acetate or ethanol, mp 145°–147° C. (dec.).

EXAMPLE 7

2-n-Butyl-4-chloro-1-[(2'-(2-triphenylmethyl-2H-tetrazol-5-yl)-1,1'-biphenyl-4-yl)methyl]-1H-imidazole-5-methanol To the reaction mixture of Example 6 was added sodium borohydride (0.1 m=3.9 g) along with some water (8.7 mL). After stirring at room temperature for 3 hours, the reaction mixture was slowly added to excess amount of water (540 ml) with stirring. The wet filter cake was washed with 270 mL of water, then crystallized from 355 g of butyl chloride to give a crude product. Recrystallization from 300 g of ethyl acetate and dried in a vacuum oven to give 49.3 g of pure title compound in 72% yield for two steps, mp 168°–169° C.

EXAMPLE 8

2-n-Butyl-4-chloro-1-[(2'-(tetrazol-5-yl)-1,1'-biphenyl-4-yl methyl]-1H-imidazole-5-methanol, potassium salt A mixture of 2-n-butyl-4-chloro-1-[(2'-(2-triphenylmethyl-2H-tetrazol-5-yl)-1,1'-biphenyl-4-yl)methyl]-1H-imidazole-5-methanol (5.3 kg) in 25L tetrahydrofuran (THF) was treated with 8.38 kg of 12% aqueous hydrochloric acid added at 23° C. over an hour. The mixture was stirred at 25° C. for 12 hours. A 30% sodium hydroxide solution was added at 22° C. over a 2-hour period until the pH was 12.5. The THF was distilled off by heating but the volume was replenished by addition of water. Distillation was terminated when the head temperature reached 94° C. The mixture was cooled to room temperature and the precipitated triphenylmethanol was removed by filtration and rinsed with water. The filtrate and rinse was extracted twice with 4L portions of toluene. Ethyl acetate (9.8L) was then added to the aqueous solution and 36% aqueous hydrochloric acid was added at 21°–24° C. until the pH was 3.8. The mixture was cooled to 10° C. and held for 1 hour. The solid was collected by filtration and washed with 50% aqueous methanol, followed by 10L ethyl acetate, then dried at 50° C. in a vacuum oven to give 2.8 kg white solid, mp 182°–183° C. (dec.). A 1.92 kg portion of this solid in 5.8 kg of isopropanol was treated with a mixture of 0.363 kg of potassium hydroxide in 185 mL water and 3.62L isopropanol at 39°–40° C. over a 4-hour period until the pH was 10. The solution was clarified by filtration. Approximately 67% of the water present was removed by distillation (monitored by Karl Fischer titration of the distillate). Heptanes (4.5L) was added and the mixture was cooled to room temperature. The product was collected by filtration and rinsed with heptanes. It was dried at 50° C. in a vacuum oven to yield 1.82 kg of white solid, mp 267°–269° C. (dec.).

EXAMPLE 9

5-(4'-Hydroxymethyl-1,1'-biphenyl-2-yl)-2-triphenylmethyl-2H-tetrazole

A mixture of 2-(2'-triphenylmethyl-2'H-tetrazol-5'-yl)phenylboronic acid (0.03 m=13.5 g), p-bromobenzyl alcohol (0.034 m=6.2 g) tetrabutylammonium carbonate (67% pure, 34 g), and 120 mL toluene in a reaction flask was evacuated and released to nitrogen three times and maintained under a nitrogen atmosphere. To the mixture was charged tetrakistriphenylphosphine palladium (0.9 mm=1.04 g). The reaction was heated at 75° to 81° C. for 5 hours. The reaction mixture was cooled to room temperature and extracted three times with 80 mL portions of water. The organic layer was clarified by 5 filtering through a Celite cake and then concentrated to a brown oil. Crystallization from about 30 mL of acetone yielded a solid which was collected and rinsed with 50% aqueous acetone. The solid was dried under a stream of nitrogen to a constant weight of 9.08 g (61.5% yield), mp 168°–170° C.

EXAMPLE 10

5-(4'-Methanesulfonyloxymethyl-1,1'-biphenyl-2-yl)-2-triphenylmethyl-2H-tetrazole To a mixture of 5-(4'-hydroxymethyl-1,1'-biphenyl-2-yl)-2-triphenylmethyl-2H-tetrazole (0.01 m=4.90 g) and potassium carbonate (0.05 m=6.90 g) stirred in 50 mL N,N-dimethylacetamide chilled at 1° C. was added a total of 3.34 g (0.024 m) of methanesulfonyl chloride in 0 portions over 6 hours. The progress of the reaction was monitored by thin layer chromatography or HPLC. The title compound was formed in better than 90% in the mixture which was used in the next example.

EXAMPLE 11

2-n-Butyl-4-chloro-1-[(2'-(2-triphenylmethyl-2H-tetrazol-5-yl)-1,1'-biphenyl-4-yl)methyl]-1H-imidazole-5-methanol To the reaction mixture of Example 10 was added 2-n-butyl-4-chloro-1H-imidazole-5-carboxaldehyde (0.01 m=1.86 g). The reaction was stirred overnight at room temperature. Water (0.87 mL) was added dropwise followed by sodium borohydride pellets (0.37 g). After stirring for 5 hours, the reaction mixture was added slowly to 100 mL water containing 3 mL acetone. The temperature was maintained at about 25° C. during the addition. The resultant slurry was stirred for an additional 45 minutes, then filtered. The solid was rinsed with two 50 mL portions of water. The wet cake was recrystallized first from 50 mL of n-butyl chloride, then from 30 mL of ethyl acetate to give 1.95 g title compound in 28% overall yield; mp 168°–169° C.

EXAMPLE 12

5-(4'-Formyl-1,1'-biphenyl-2-yl)-2-triphenylmethyl-2H-tetrazole 2-(2'-Triphenylmethyl-2'H-tetrazol-5'-yl)phenyl boronic acid (5 mm=2.16 g), p-bromobenzaldehyde (6 mm=1.12 g), potassium carbonate (10 mm=1.38 g), tetrabutylammonium bromide (0.46 mm=0.15 g), toluene (20 mL), and water (1.2 mL) were charged to the reaction flask. The system was evacuated and released to nitrogen three times and then maintained under a nitrogen atmosphere. Tetrakistriphenylphosphine palladium (0.15 mm=0.18 g) was charged to the reaction mixture which was then heated at 70° to 80° C. for 5.5 hours. The cool reaction mixture was filtered to remove some solid; rinsed with toluene and water. The filtrate and rinsings were combined. The organic layer was separated and washed with 10 mL water, then dried over magnesium sulfate, filtered, and concentrated. The residue was triturated with a mixture of 8 mL toluene and 5 mL n-heptane. The solid was collected by filtration, rinsed with 1:1 toluene/n-heptane, and dried under vacuum is 1.18 g (48% yield), mp 147°–149° C.

EXAMPLE 13

5-(4'-Hydroxymethyl-1,1'-biphenyl-2-yl)-2-triphenyl-methyl-2H-tetrazole 5-(4'-formyl-1,1'-biphenyl-2-yl)-2-triphenylmethyl-2H-tetrazole was dissolved in N,N-dimethylacetamide and some water and reduced by sodium borohydride. The reaction mixture was then poured into water slowly to precipitate the title compound which is further purified by recrystallizations as described in Example 11.

EXAMPLE 14

2-n-Butyl-4-chloro-1-p-bromobenzyl-1H-imidazole-5-carboxaldehyde

A mixture of 2-n-butyl-4-chloro-1H-imidazole-5-carboxaldehyde (0.6 m=111.9 g), p-bromobenzylbromide (0.6 m=153.02 g), anhydrous potassium carbonate (0.75 m=103.5 g), and dry N,N-dimethylacetamide (900 mL) was stirred at room temperature for 4 hours. The mixture was diluted with 1.2L of toluene and 1.8L of water. After mixing for half an hour, the layers were separated. The organic layer was washed two more times with 900 mL portions of water, then dried over magnesium sulfate. The drying agent was removed by filtration and the filtrate was concentrated. The residual oil was pumped overnight to a weight of 191.71 g (89.9% yield).

EXAMPLE 15

2-n-Butyl-4-chloro-1-[(2'-(2-triphenylmethyl-2H-tetrazol-5-yl)-1,1'-biphenyl-4-yl)methyl]-1H-imidazole-5-methanol A mixture of the oil obtained in Example 14 (0.05 m=17.8 g), 2-(2'-triphenylmethyl-2'H-tetrazol-5'-yl)phenylboronic acid (0.065 m=29.3 g), potassium carbonate (0.1 m=13.8 g), water 11 mL), tetra-n-butylammonium bromide (0.005 m=1.61 g), triphenylphosphine (0.006 m=1.58 g) in 200 mL toluene was evacuated and released to nitrogen three times and maintained under a nitrogen atmosphere. Tris(dibenzylideneacetone)dipalladium (1.5 mm=0.64 g) was charged and the reaction was heated at 75° to 81° C. for 12 hours. The cooled reaction mixture was filtered to remove some grey solid. The toluene layer was stirred with sodium borohydride (0.1 m=3.8 g), tetra-n-butyl ammonium bromide (0.005 m=1.6 g), and 30 mL water for six hours. The mixture was filtered through a Celite cake to remove the black tarry precipitate. The organic layer was washed once with 100 mL water then stirred with a solution of thiourea (7 g) in 100 mL water for 1 hour. Some brown sludge (palladium complex) was formed and precipitated out. The mixture was filtered and the organic layer was separated then treated with a fresh solution of thiourea (7 g) in 100 mL water for 1 hour. The organic layer was separated, washed once with 100 mL water and once with 100 mL saturated sodium chloride solution. The organic layer was stirred with 30 g magnesium sulfate and 15 g charcoal for 1 hour. The solid was removed by filtering through a Celite cake. The filtrate was concentrated to an oil and crystallized from 35 mL of isobutyl acetate in an ice bath. The solid was collected and dried under a stream of nitrogen to a constant weight of 17.17 g.

EXAMPLE 16

2-n-Propyl-4-ethyl-1-[(2'-(2-triphenylmethyl-2H-tetrazol-5-yl)-1,1'-biphenyl-4-yl)methyl]-1H-imidazole-5-carboxaldehyde Starting with 2-n-propyl-4-ethyl-1H-imidazole-5-carboxaldehyde and using the procedure of Example 14 and then the procedure of Example 15, the title compound is prepared.

EXAMPLE 17

2-n-Propyl-4-pentafluoroethyl-1-[(2'-(2-triphenylmethyl-2H-tetrazol-5-yl)-1,1'-biphenyl-4-yl)methyl]-1H-imidazole-5-carbomethoxylate Starting with 2-n-propyl-4-pentafluoroethyl-1H-imidazole-5-carbomethoxylate and using the procedure of Example 14 and then the procedure of Example 15, the title compound is prepared.

EXAMPLE 18

2-n-butyl-4-chloro-5-hydroxymethyl-1-p-bromobenzyl-1H-imidazole

A suspension of 2-n-butyl-4-chloro-1H-imidazole-5-carboxyaldehyde (146.9 g, 0.78 mol) and p-bromobenzyl bromide (195 g, 0.78 mol) in dimethylacetamide (1.0L) was cooled to 0° C. and potassium carbonate (138 g, 1.0 mol) was added. The mixture was aged for three hours at 0° C. and then at 20° to 25° C. for two to four hours. The mixture was diluted with dimethylacetamide (0.15L) and then filtered. The filter cake was washed with dimethylacetamide (50 ml). The combined filtrates were diluted with methanol (0.66L) and cooled to 0° C. Sodium borohydride (37.8 g, 1.0 mol) was added as a solid and the mixture was aged with stirring at 20° to 25° C. for two hours. Water (1.56L) was added slowly to crystallize the product. The filter cake was washed carefully with water (1.56L) and dried in vacuo at 60° C. The yield was 255 g (91%, corrected for 99.5% purity).

EXAMPLE 19

2-n-Butyl-4-chloro-1-[(2'-(2-triphenylmethyl-2H-tetrazol-5-yl)-1,1'-biphenyl-4-yl)methyl]-1H-imidazole-5-methanol All operations described for this example were performed under an atmosphere of nitrogen.

Catalyst Preparation

To a mixture of palladium chloride (10.6 mg) and triphenylphosphine (31.5 mg) was added anhydrous toluene (4 ml). The heterogeneous solution was degassed by vacuum/nitrogen purges (3×) and then heated to 60° C. for 30 minutes. Triisopropylphosphite (30.0 microliters) was added and the mixture was further heated at 60° C. until a homogeneous solution was obtained (1 to 2 hours).

Coupling 2-(2'-triphenylmethyl-2'H-tetrazol-5'-yl)phenylboronic acid (1.3 g) was suspended in toluene (4 ml) and water (100 microliters) was added. The heterogeneous mixture was stirred at room temperature for 30 minutes and potassium carbonate (0.7 g) was then charged followed by the titled product of Example 18 (0.7 g). The mixture was degassed via vacuum/nitrogen purges (3×) and the above catalyst solution was added. The temperature of the mixture was raised to 80° to 85° C. and kept at this temperature for 2 hours. After the mixture was cooled to 40° C., water (5 ml) was added. The aqueous layer was removed and the organic phase was concentrated in vacuo at ≦30° C. to a volume of ~3 ml. Methyl i-butyl ketone (MIBK) (8 ml) was added and the mixture was again reduced to ~3 ml. The mixture was diluted with MIBK (4 ml) and water (36 microliters), heated to 60° C. and then cooled and aged first at 0° C. for 30 minutes followed by aging at −10° C. with stirring for 2 hours. The crystallized product was collected by filtration as a mono-MIBK solvate (1.44 g, 94% yield). The crude product was dissolved in MIBK (2.1 ml) at 80° C., the solution was filtered hot at 80° C. and water (33.8 microliters) was added. The solution was cooled slowly to 0° C. over 1 hour and aged at 0° C. for 30 minutes followed by aging at −10° C. with stirring for 2 hours. After filtration 1.38 g of the mono-MIBK solvated product was recovered (90% yield).

EXAMPLE 20

2-n-Butyl-4-chloro-1-[(2'-(2-triphenylmethyl-2H-tetrazol-5-yl)-1,1'-biphenyl-4-yl)methyl]-1H-imidazole-5-methanol All operations described for this example were performed under an atmosphere of nitrogen.

Catalyst Preparation

The following two procedures can be used with similar results.

Procedure A

To a mixture of palladium chloride (354 mg) and triphenylphosphine (2.1 g) was added anhydrous tetrahydrofuran (THF) (75 ml). The heterogeneous solution was degassed by vacuum/nitrogen purges (3×) and then refluxed for 4 hours.

Most of the palladium chloride changed over to bis(triphenylphosphine)palladium chloride during the reflux. Some insoluble black solids were still observed at this point.

The heterogeneous THF solution containing the phosphinated palladium chloride was cooled to room temperature and diethylzinc (4.0 ml, 1M in hexanes) was added. Except for a small amount of black solids, the solution essentially became homogeneous after stirring for 30 minutes. This activated catalyst solution was used in the coupling step described below.

Procedure B

To a mixture of palladium chloride (354 mg) and triphenylphosphine (2.1 g) was added anhydrous THF (75 ml). The heterogeneous solution was degassed by vacuum/nitrogen purges (3×) and then triisopropylphosphite (0.99 ml) was added. The mixture was maintained at room temperature until all the palladium chloride was dissolved and a homogeneous solution was obtained (0.5 to 1 hour).

Benzyltrimethylammonium Carbonate Preparation

To a benzyltrimethylammonium hydroxide solution (42 g) was added ammonium carbonate (5.0 g) and the reaction was aged with stirring until all of the ammonium carbonate dissolved (~30 minutes). The methanol solvent was removed in vacuo and further displaced with THF (3×10 ml). The residual carbonate was dissolved in THF (90 ml).

Coupling Step

To the above carbonate solution was charged the titled product of Example 1 (24.0 g) and the titled product of Example 18 (14.2 g). The mixture was degassed by vacuum/nitrogen purges (5×), followed by the addition of the catalyst solution prepared above. The reaction mixture was heated to reflux, aged until completion (8 to 10 hours), cooled to room temperature and filtered through a pad of Celite. The Celite was further washed with THF (3×10 ml). The yield was 89 wt %.

EXAMPLE 21

2-n-Butyl-4-chloro-1-[(2'-(tetrazol-5-yl)-1,1'-biphenyl-4-yl)methyl-1H-imidazole-5-methanol, potassium salt 2-n-butyl-4-chloro-1-[2'-(2-triphenylmethyl-2H-tetrazol-5-yl)-1,1'-biphenyl-4-yl)methyl]-1H-imidazole-5-methanol (5.0 g, 6.54 mmol) was dissolved in THF (60 ml). 4N Sulfuric acid (38 ml, 152 mmol) was added with stirring at 25° to 30° C. The solution was aged overnight at 20° to 25° C. and isopropyl acetate (60 ml) was then added. The layers were separated and the organic phase was back-extracted with 4N sulfuric acid (19 ml). The aqueous layers were combined and the organic solvents (THF and isopropyl acetate) were removed in vacuo. The remaining aqueous solution was diluted with THF (10% of THF by volume) and passed through a pad of Ecosorb S 402 (5.0 g). The pad was rinsed with 10% THF in 4N sulfuric acid. The filtrate was then passed through a column of SP-207 (60 ml) and the column was washed with water (180 ml) followed with 1M $K_2HPO_4$ (180 ml). The pH of the eluent was monitored to ensure complete potassium salt formation. Further washing with water (180 ml) removed the sulfate and excess phosphate. The potassium salt product was eluted with 20% aqueous THF. Concentration of the aqueous solution and dilution with isopropanol gave crystalline product. Alternatively, the product was isolated by spray drying. The yield was 2.56 g (85%).

EXAMPLE 22

1-Bromo-4-(2'-n-butyl-4'-chloro-5'-hydroxymethylimidazole-1'H-1'-yl)methylbenzene

I. Alkylation

To 200 mL of dimethyl acetamide under a nitrogen atmosphere in a 1-liter 3-necked flask fitted with a mechanical stirrer and thermocouple is charged 30.8 g (0.163 mol) of 2-n-butyl-4-chloro-5-formyl-1H-imidazole 1 and 43.7 g (0.16 mol) of 4-bromobenzyl bromide 2. The solution is cooled to −5° C. followed by portionwise addition of 27.1 g (0.19 mol) of powdered potassium carbonate over 10 min with rapid stirring while keeping the reaction temperature between −5°–0° C. The slurry is stirred at −5° C. for 2 h and room temperature for 2 h or until the alkylation is complete.

II. Filtration

The slurry is filtered and the cake is washed with an anhydrous mixture of dimethyl acetamide (30 mL) and methanol (130 mL). The filtrate is used directly in the next step.

III. Reduction

Under a nitrogen atmosphere, 1.85 g (48 mmol) of powdered sodium borohydride is added portionwise over 0.5 h to the filtrate at −15° C. in a 5-liter 3-necked flask with a mechanical stirrer and a thermocouple, keeping the reaction temperature between −15° to −5° C. The mixture is warmed to room temperature and aged for 1 h or until the reduction is complete.

IV. Crystallization

Acetic acid (2.74 mL) is added dropwise over 10 min with rapid stirring while keeping the temperature of the mixture at 20°-25° C. This mixture is aged at room temperature for 0.5 h, followed by the addition of water (160 mL) dropwise over 1 h. The solution is seeded with imidazole 4 and followed by the addition of water (160 mL) dropwise over 1 h. The product precipitated within 0.5 h. The slurry is aged at room temperature for 2 h, cooled to 10° C., aged for 0.5 h and the solid is filtered. The cake is washed with 320 mL of water, suction dried under nitrogen at room temperature for 2 h and oven dried under house vacuum (−24 psi) at <60° C. for 12 h to afford 54.3 g of imidazole 4 as a white solid (HPLC assay: 98.8 A %, 97.2 W %, overall yield: 92.4%, 0.5 W % of the regioisomer).

EXAMPLE 23

2-n-Butyl-4-chloro-1-[(2'-(2-triphenylmethyl-2H-tetrazol-5-yl)-1,1'-biphenyl-4-yl)methyl]-1H-imidazole-5-methanol I. Catalyst Preparation Triphenylphosphine (262 mg, 1.0 mmol) is dissolved in THF (20 mL) and the solution is degassed by vacuum/nitrogen purges (3×). Palladium acetate (56 mg, 0.25 mmol) is added and the solution is degassed again (3×). The resulting solution is warmed to 60° C. for 30 min. and then cooled to 25° C.

II. Coupling

Note: All solvents must be degassed.

2-(2'-triphenylmethyl-2'H-tetrazol-5'-yl)phenylboronic acid (15.4 g, 26.7 mmol, 75 wt % pure) is suspended in diethoxymethane (DEM) (80 mL, KF≦500 mg/ml). Water (0.55 mL, 31 mmol) is added and the slurry is aged at ambient temperature for 30 min. After the age, another charge of water (0.55 ml, 31 mmol) is added to the boronic acid suspension under agitation. The slurry is then treated with powdered potassium carbonate (8.6 g, 62 mmol) and alkylated imidazole, the titled product of Example 22 (8.97 g, 25 mmol). The mixture is aged at 20°-25° C. for 30 min then degassed well (3×). (Note: in the pilot plant, degassing takes much longer and can be started immediately after the imidazole and carbonate are added). The catalyst solution is then charged and the mixture is heated to reflux (76°-79° C.). The reaction is complete in 2-6 hours. When the imidazole has been consumed, water (30 mL) and THF (25 ml) are added and the mixture is stirred at 55°-60° C. The water layer is separated and the organic layer is washed with water (30 mL). The organic layer is concentrated in vacuo to a volume of 50 ml to remove most of the THF. More DEM (50 ml) is added and removed by distillation to further reduce THF to ≦5 vol %. The residual organic solution is diluted with warm (60° C.) DEM (to a final volume of 75 ml) and water (0.5 ml, 28 mmol). The mixture is then cooled slowly to −12° C. over 2 hours. After aging at −12° C. for 1 hour, the product is collected by filtration. The cake is washed with cold DEM (25 mL). Vacuum drying at 40° C. gave 15.5 g (93% of the titled product (non-solvated). [Pd=600 to 1000 ppm.].

EXAMPLE 24

2-n-Butyl-4-chloro-1-[(2'-(2-triphenylmethyl-2H-tetrazol-5-yl)-1,1'-biphenyl-4-yl)methyl]-1H-imidazole-5-methanol I. Catalyst Preparation Triphenylphosphine (262 mg, 1.0 mmol) is dissolved in THF (20 mL) and the solution is degassed by vacuum/nitrogen purges (3×). Palladium acetate (56 mg, 0.25 mmol) is added and the solution is degassed again (3×). The resulting solution is warmed to 60° C. for 30 min. and then cooled to 25° C.

II. Coupling

Note: All solvents must be degassed.

2-(2'-Triphenylmethyl-2'H-tetrazol-5'-yl)phenylboronic acid (15.4 g, 26.7 mmol, 75 wt % pure) is suspended in diethoxymethane (DEM) (80 mL, KF≦500 mg/ml). Water (0.55 mL, 31 mmol) is added and the slurry is aged at ambient temperature for 30 min. After the age, another charge of water (0.55 ml, 31 mmol) is added to the boronic acid suspension under agitation. The slurry is then treated with powdered potassium carbonate (8.6 g, 62 mmol) and the titled product of Example 22, the alkylated imidazole (8.97 g, 25 mmol). The mixture is aged at 20°-25° C. for 30 min then degassed well (3×). (Note: in the pilot plant, degassing takes much longer and can be started immediately after the imidazole and carbonate are added). The catalyst solution is then charged and the mixture is heated to reflux (76°-79° C.). The reaction is complete in 2-6 hours. When the imidazole has been consumed, water (30 mL) and THF (25 ml) are added and the mixture is stirred at 55°-60° C. The water layer is separated and the organic layer is washed with water (30 mL). Tributylphosphine (0.62 ml, 10 mol %) is added and the organic layer is concentrated in vacuo to a volume of 50 ml to remove most of the THF. More DEM (50 ml) is added and removed by distillation to further reduce THF to ≦5 vol %. The residual organic solution is diluted with warm (60° C.) DEM (to a final volume of 75 ml) and water (0.5 ml, 28 mmol). The mixture is then cooled slowly to −12° C. over 2 hours. After aging at −12° C. for 1 hour, the product is collected by filtration. The cake is washed with cold DEM (25 mL). Vacuum drying at 40° C. gave 15.5 g (93%) of the titled product (non-solvated). [Pd≦10 ppm].

EXAMPLE 25

2-n-Butyl-4-chloro-1-[(2'-(2-triphenylmethyl-2H-tetrazol-5-yl)-1,1'-biphenyl-4-yl)methyl]-1H-imidazole-5-methanol as the methyl isobutyl ketone solvate A suspension of the titled product of Example 24 (5 g) in methyl isobutyl ketone (MIBK) (40 ml) is degassed (3×) and tributylphosphine (0.12 g, 8 mol %) is added. The mixture is heated to 85° C. at which time a homogeneous solution was obtained. Degassed water (0.135 g, 100 mol %) is then added and the solution is cooled to −10° C. over 2 hours. The heterogeneous solution is aged at −10° C. for 2 hours, the crystallized product is collected by filtration and washed with cold MIBK (−10° C., 15 ml). The recovery was 5.40 g of the titled product 93.9%, as the MIBK solvate).

EXAMPLE 26

2-n-butyl-4-chloro-1-[(2'-(tetrazol-5-yl)-1,1'-biphenyl-4-yl)-methyl]-1H-imidazole-5-methanol, potassium salt

I. Deprotection

Dissolve 2.50 g of the titled product of Example 25, the methyl isobutyl ketone solvate, by adding 10 mL of 0.75M H$_2$SO$_4$ in 50:50 MeCN:water. Age 2 hours 25 min, 23°–25° C. Add 15 mL of water in 2 min (can be added in 30 min to an hour in larger scales), and age 1.75 hours, 23°–25° C. Filter and wash with 5 mL of 20:80 MeCN:water. There was almost no starting material left in the trityl alcohol filter cake (<0.05 area %).

II. Free Acid Formation

Dilute the above filtrate with 13 mL of MeCN. The pH of the solution is 1.50. The temperature of the solution following neutralization and crystallization was 22°–24° C. After adding 1.5 mL of 3N NaOH (pH 1.75–1.65), the reaction is seeded with 20 mg of the free acid. Age 15 min. Slowly add the next 1 mL of 3M NaOH to allow for good crystal growth (on this scale, the addition time was 5–10 min). Age 30 min. Add the remaining 3M NaOH (pH 3.60–3.50). Age 1 hour. The white slurry is filtered and washed with 5 mL of 20:80 MeCN:water then 10 mL of water. A thorough water wash of the free acid filter cake is necessary to remove all the salts. The wash can be checked for SO$_4^{-2}$. The filter cake is dried in a vacuum oven at 35° C. for 18 hours with nitrogen purge. The yield of the free acid was 1.28 g (92.5%) and there was 54 mg (4%) of the free acid in the mother liquors.

III. Salt Formation

To 4.0 g (9.46 mmoles) of the free acid is added 10.9 ml of 0.842N KOH solution all in one portion. The slurry is aged at room temperature for 30 minutes, during which time most of the solid dissolves. The cloudy solution is filtered and the solids collected on a sintered glass funnel. The pH of the filtrate is measured at 9.05. The aqueous solution is added slowly to a refluxing azeotropic mixture of cyclohexane/isopropanol (69° C.) whereupon the ternary azeotrope cyclohexane/isopropanol/water (64° C.) begins to distill. When the solution is dry the temperature of the overhead rises to 69° and the potassium salt crystallizes. When the water content of the pot is <0.05% the distillation is halted and the white slurry is cooled to room temperature. The white crystalline solid is collected on a sintered glass funnel and washed with 10–15 ml of cyclohexane/isopropanol 67/33 and dried in a vacuum oven (wt 3.8 g yield 95%).

What is claimed is:

1. A process for preparing a compound of formula II

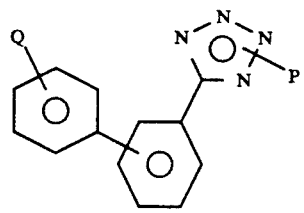

which comprises the following steps:

(a) mixing a compound of formula I

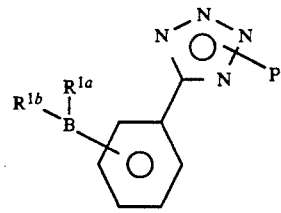

wherein:

P is triphenylmethyl, tertiary-butyl, C$_1$-C$_4$ alkoxymethyl, methylthiomethyl, phenyl C$_1$-C$_4$ alkoxymethyl, p-methoxybenzyl, 2,4,6-trimethylbenzyl, 2-(trimethylsilyl)ethyl, tetrahydropyranyl, piperonyl, or benzenesulfonyl; and R$^{1a}$ and R$^{1b}$ are each independently chlorine, bromine, C$_1$-C$_4$ alkoxy, hydroxy, or R$^{1a}$ and R$^{1b}$ can be taken together with B to form a structure:

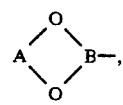

A is phenyl, or (CH$_2$)$_n$, n is 2–4, with coupling solvent(s), wherein the coupling solvent(s) is(are) selected from the group consisting of benzene, toluene, ethyl ether, tetrahydrofuran, dioxane, acetonitrile, dimethylformamide, dimethylacetamide, dimethylsulfoxide, ethanol, methanol, propanol, water, 2-methyl-tetrahydrofuran or diethoxymethane;

(b) mixing into the reaction mixture of step (a), a base, wherein the base is selected from:

(i) an organic tertiary non-nucleophilic base, wherein the organic tertiary non-nucleophilic base is selected from the group consisting of triethylamine or diisopropylethylamine, (ii) an inorganic base, wherein the inorganic base is selected from potassium carbonate, sodium carbonate, cesium carbonate, thallium hydroxide, potassium alkoxide or sodium alkoxide, and (iii) an organic solvent soluble base, wherein the organic solvent soluble base is selected from the group consisting of tetra-n-butylammonium carbonate, tetra-n-butylammonium hydroxide, benzyltrimethylammonium carbonate, benzyltrimethylammonium methyl carbonate, benzyltrimethylammonium methoxide, or benzyltrimethylammonium hydroxide;

and a compound having the formula:

X is bromine, iodine, methanesulfonyloxy, toluenesulfonyloxy, fluorosulfonyloxy, or trifluoromethanesulfonyloxy; and Q is hydrogen, methyl, C$_1$-C$_4$ alkyl, hydroxymethyl, triorganosilyloxymethyl, hydroxy C$_1$-C$_4$ alkyl, formyl, C$_1$-C$_4$ acyl, C$_1$-C$_4$ alkoxycarbonyl, or W-L—;

L is a single bond, —(CH$_2$)$_t$—, —(CH$_2$)$_t$O(CH$_2$)$_r$—, or —(CH$_2$)$_r$S(O)$_x$(CH$_2$)$_r$—, t is 1 to 4;

r is 0 to 2; and

W is a mono-, bi-, or multi-cyclic heteroaromatic group, which may be partially or completely hydrogenated, in which each ring member of said group includes at least 1 carbon atom and from 1 to 5 heteroatoms;

(c) charging the reaction mixture of step (b) with a metal catalyst, wherein the metal catalyst is selected from the group consisting of nickel complex, palladium complex or platinium complex, for one to thirty hours at a temperature ranging from room temperature to 150° C.;

(d) purifying the reaction mixture (c) containing the compound of formula II to give the purified compound of formula II; and (e) recrystallizing the purified compound of formula II with a recrystallizing solvent.

2. The process of claim 1 wherein the metal catalyst is a palladium complex selected from bis(dibenzylideneacetone)palladium (0), tris(dibenzylideneacetone)dipalladium(0), tetrakis(triphenylphosphine)palladium (0) or a phosphinated palladium(II) complex.

3. The process of clam 2 wherein the palladium complex is a phosphinated palladium II complex selected from the group consisting of bis(triphenylphosphine)palladium chloride, bis(triphenylphosphine)palladium bromide, bis(triphenylphosphine)palladium acetate, bis(triisopropylphosphite)palladium chloride, bis(triisopropylphosphite)palladium bromide, bis(triisopropylphosphite)palladium acetate, [1,2-bis(diphenylphosphino)ethane]palladium chloride, [1,2-bis(diphenylphosphino)ethane]palladium bromide, [1,2-bis(diphenylphosphino)ethane]palladium acetate, [1,3-bis(diphenylphosphino)propane]palladium chloride, [1,3-bis(diphenylphosphino)propane]palladium bromide, [1,3-bis(diphenylphosphino)propane]palladium acetate, [1,4-bis(diphenylphosphino)butane]palladium chloride, [1,4-bis(diphenylphosphino)butane]palladium bromide and [1,4-bis(diphenylphosphino)butane]palladium acetate.

4. The process of claim 2 wherein the palladium complex is generated in the reaction mixture in the presence of a catalyst forming solvent, wherein the catalyst forming solvent(s) is(are) selected from the group consisting of benzene, toluene, ethyl ether, tetrahydrofuran, dioxane, acetonitrile, dimethylformamide, dimethylacetamide, dimethyl sulfoxide, ethanol, methanol, propanol, water, 2-methyl-tetrahydrofuran and diethoxymethane.

5. The process of claim 4 wherein the catalyst forming solvent is tetrahydrofuran or a mixture of tetrahydrofuran and dimethoxymethane.

6. The process of claim 4 wherein the catalyst forming solvent is toluene.

7. The process of claim 4 wherein the palladium complex is tetrakis(triphenylphosphine)palladium (O).

8. The process of claim 4 wherein tetrakis(triphenyl phosphine)palladium(O), is generated in the reaction mixture by contacting a complex of tris(dibenzylideneacetone)dipalladium(O) and triphenylphosphine in tetrahydrofuran.

9. The process of claim 4 wherein bis(triphenylphosphine)palladium chloride is generated in the reaction mixture by contacting palladium chloride and triphenylphosphine in tetrahydrofuran.

10. The process of claim 5 wherein tetrakis(triphenylphosphine)palladium (0) is generated in the reaction mixture by contacting palladium chloride, triphenylphosphine and diethylzinc in tetrahydrofuran.

11. The process of claim 5 wherein bis(triphenylphosphine)palladium acetate is generated in the reaction mixture by contacting palladium acetate and triphenylphosphine in the catalyst forming solvent with or without heat.

12. The process of claim 1 wherein the organic tertiary non-nucleophilic base is triethylamine.

13. The process of claim 1 wherein the inorganic base is potassium carbonate.

14. The process of claim 1 wherein the organic solvent soluble base is tetra-n-butylammonium carbonate.

15. The process of claim 1 wherein the organic solvent soluble base is benzyltrimethylammonium carbonate.

16. The process of claim 14 wherein the organic solvent soluble base is tetra-n-butylammonium carbonate which is generated in the reaction mixture by reacting potassium carbonate with tetra-n-butylammonium bromide in the presence of toluene-water.

17. The process of claim 15 wherein the organic solvent soluble base is benzyltrimethylammonium carbonate which is generated in the reaction mixture by reacting benzyltrimethylammonium hydroxide with ammonium carbonate in the presence of methanol.

18. The process of claim 1 wherein the coupling solvent is a mixture of tetrahydrofuran and diethoxymethane.

19. The process of claim 1 wherein the coupling solvent is toluene.

20. The process of claim 1 wherein the purification step includes tributylphosphine.

21. The process of claim 1 wherein the recrystallization solvent is methyl isobutyl ketone, or a mixture of tetrahydrofuran and diethoxymethane.

22. The process of claim 1 wherein Q is W-L, where L is —CH$_2$— and W is

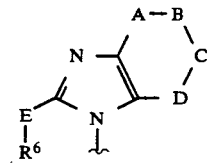

E is a single bond, —NR$^{13}$(CH$_2$)$_s$—, —S(O)$_x$—(CH$_2$)$_s$— where x is 0 to 2 and s is 0 to 5, —CH(OH)—, —O—, —CO—;

R$^6$ is (a) phenyl or naphthyl optionally substituted with 1 or 2 substituents selected from the group consisting of halo (Cl, Br, I, F), —O—C$_1$-C$_4$ alkyl, —C$_1$-C$_4$ alkyl, NO$_2$, CF$_3$, —SO$_2$NR$^9$R$^{10}$, —S—C$_1$-C$_4$ alkyl, —OH, NH$_2$, —C$_3$-C$_7$ cycloalkyl, —C$_3$-C$_{10}$-alkenyl;

straight chain or branched C$_1$-C$_9$-alkyl, C$_2$-C$_6$-alkenyl or C$_2$-C$_6$-alkynyl each of which can be optionally substituted with a substituent selected from the group consisting of aryl, where aryl is phenyl or naphthyl optionally substituted with one or two substituents selected from the group consisting of halo(Cl, Br, I, F), C$_1$-C$_4$-alkyl, C$_1$-C$_4$-alkoxy, NO$_2$, CF$_3$, C$_1$-C$_4$-alkylthio, OH, $NH_2$, $NH(C_1-C_4\text{-alkyl})$, $N(C_1-C_4\text{-alkyl})_2$, $CO_2H$, and $CO_2-C_1-C_4\text{-alkyl}$; $C_3-C_7$-cycloalkyl; halo(Cl, Br, I, F); —OH; —$NH_2$; —NH(-$C_1-C_4$-alkyl); —$CF_2CF_3$; —$N(C_1-C_4\text{-alkyl})_2$; —NH—$SO_2R^4$; —$COOR^4$; —$CF_3$; —$CF_2CH_3$; —$SO_2NHR^9$; or (c) an unsubstituted, monosubstituted or disubstituted aromatic 5 to 6 membered cyclic ring which can contain one or two members selected from the group consisting of N, O, S, and wherein the substituents are members selected from the group consisting of —OH, —SH, $C_1-C_4$-alkyl, $C_1-C_4$-alkyloxy $CF_3$, Halo(Cl, Br, I, F), or $NO_2$, (d) perfluoro-$C_1-C_4$-alkyl, (e) $C_3-C_7$-cycloalkyl optionally mono- or disubstituted with $C_1-C_4$-alkyl or $CF_3$;

$R^4$ is H, straight chain or branched $C_1-C_6$-alkyl, aryl or —$CH_2$-aryl where aryl is as defined above;

$R^9$ is H, $C_1-C_5$-alkyl, aryl or —$CH_2$-aryl where aryl is as defined above;

$R^{10}$ is H, $C_1-C_4$-alkyl;

$R^{13}$ is H, —CO($C_1-C_4$-alkyl), $C_1-C_6$-alkyl, allyl, $C_3-C_6$-cycloalkyl, phenyl or benzyl;

—A—B—C—D— represents the constituent atoms of a 6-member unsaturated heterocyclic ring with the imidazole to which they are attached containing 1 to 3 nitrogen atoms and includes the following:

1. 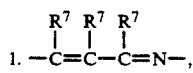
2. 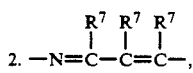
3. 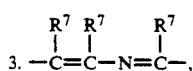
4. 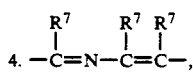
5. 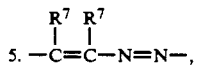
6. 
7. 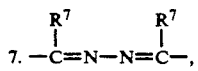
8. 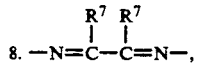
9. 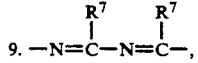
10. 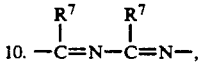
11. 

-continued

12. 
13. 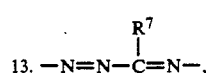
14. 
15. 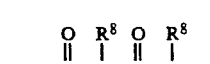
16. 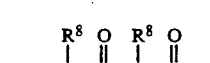
17. 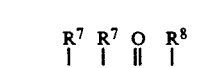
18. 
19. 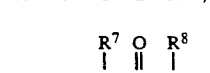
20. 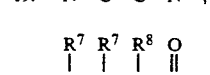
21. 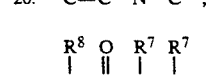
22. 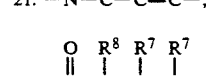
23. 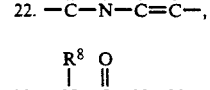
24. 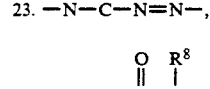
25. 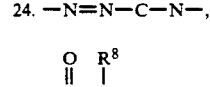
26. 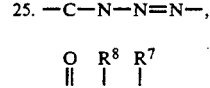
27. 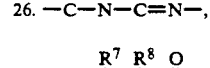
28. 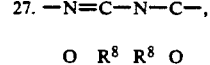
29. 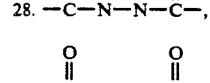
30. 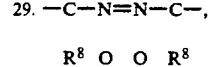
31. 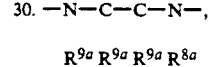

-continued

32. 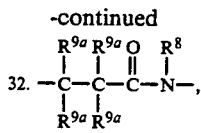

33. 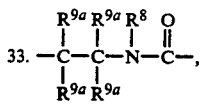

34. 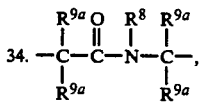

35. 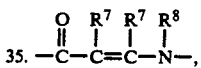

36. 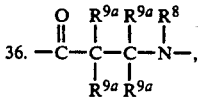

37. 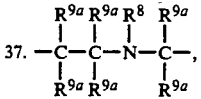

wherein:
$R^7$ groups can be the same or different and represent:
a) hydrogen,
b) $C_1$-$C_6$ straight or branched chain alkyl, or $C_2$-$C_6$ alkenyl, or alkynyl each of which is unsubstituted or substituted with:
  i) —OH,
  ii) —$C_1$-$C_4$-alkoxy,
  iii) —$CO_2R^4$,
  iv) —$COR^4$, v)
  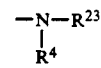

vi) —$CON(R^4)_2$, vii)
  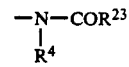

viii) —$N(R^4)_2$,
  ix) —aryl as defined above,
  x) —heterocyclic as defined in (O) below,
  xi) —$S(O)_xR^{23}$,
  xii) —tetrazol-5-yl,
  xiii) —$CONHSO_2R^{23}$,
  Xiv) —$SO_2NH$-heteroaryl,
  (xv) —$SO_2NHCOR^{23}$,

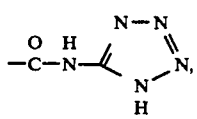

-continued xvii) 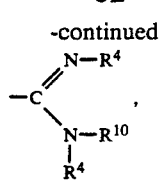

xviii) 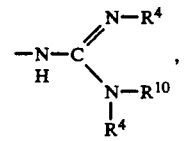

xix) —$PO(OR^4)_2$,
xx) —$PO(OR^4)R^9$,
c) halo, such as chloro, bromo or iodo,
d) perfluoro-$C_1$-$C_4$-alkyl,
e) —OH,
f) —$NH_2$, g)
$$-\underset{R^4}{N}-R^{23}$$

h)
$$-\underset{R^4}{N}-COR^{23}$$

i) —$OR^{23}$,
j) —$CO_2R^4$,
k) —$CON(R^4)_2$,
l) —NH—$C_3$-$C_7$-cycloalkyl,
m) —$C_3$-$C_7$-cycloalkyl,
n) aryl as defined above, or
o) heterocyclic which is a five- or six-membered saturated or unsaturated ring containing up to three heteroatoms selected from the group consisting of O, N, or S wherein S may be in the form of sulfoxide or sulfone and which may be optionally substituted with one or two substituents which are members selected from the group consisting of halo (Cl, Br, F, I), $C_1$-$C_4$-alkyl, $C_1$-$C_4$-alkoxy, $C_1$-$C_4$-S(O)$_x$— where x is as defined above, $CF_3$, $NO_2$, OH, $CO_2H$, $CO_2$-$C_1$-$C_4$-alkyl, $NH_2$, $NH(C_1$-$C_4$-alkyl) or $N(R^4)_2$;
p) —CN,

where n is 4 to 6,
r) —$SO_2N(R^4)_2$,
s) —tetrazol-5-yl,
t) —$CONHSO_2R^{23}$,
u) —$PO(OR^4)_2$,
v) —$NHSO_2CF_3$,
w) —$SO_2NH$-heteroaryl,
x) —$SO_2NHCOR^{23}$,
y) —$S(O)_xR^{23}$,

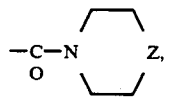

aa) —PO(OR$^4$)R$^9$,
bb) —NHSO$_2$R$^{23}$,
cc) —NHSO$_{2NH}$R$^{23}$,
dd) —NHSO$_{2NHCO}$R$^{23}$,
ee) —NHCONHSO$_2$R$^{23}$, $$\begin{array}{c} R^4 \quad R^4 \\ | \quad\quad | \\ -N-C-N-R^{23}, gg) \\ \| \\ O \end{array}$$

hh) —CO-aryl, $$-\underset{O}{\overset{H}{C-N}}-\underset{\underset{H}{N}}{\overset{N-N}{\diagup\diagdown}}N, \quad \text{ii)}$$

jj) —CO—C$_1$-C$_4$-alkyl,
kk) —SO$_2$NH—CN, $$-C\diagup\diagdown\overset{N-R^4}{\underset{\underset{R^4}{N-R^{10}}}{}}, \quad \text{ll)}$$

$$-\underset{H}{N}-C\diagup\diagdown\overset{N-R^4}{\underset{\underset{R^4}{N-R^{10}}}{}}, \quad \text{mm)}$$

R$^8$ groups can be the same or different and represent:
  a) hydrogen
  b) C$_1$-C$_5$-alkyl or alkenyl either substituted or unsubstituted with C$_1$-C$_5$-alkoxy, —N(R$^4$)$_2$, —COR$^4$ or C$_3$-C$_5$-cycloalkyl,
  c) C$_3$-C$_5$-cycloalkyl,
R$^{8a}$ is R$^8$ or C$_1$-C$_4$-acyl;
R$^{9a}$ groups can be the same or different and represent:
  a) hydrogen,
  b) C$_1$-C$_5$-alkyl or alkenyl either substituted or unsubstituted with
    i) hydroxy,
    ii) —CO$_2$R$^4$,
    iii) —CONHR$^4$, or
    iv) —CON(R$^4$)$_2$;
R$^{23}$ is (a) aryl as defined above,
  (b) heteroaryl, wherein heteroaryl is an unsubstituted, monosubstituted or disubstituted five- or six-membered aromatic ring which can optionally contain 1 to 3 heteroatoms selected from the group consisting of O, N, or S and wherein the substitutents are members selected from the group consisting of —OH, —SH, —C$_1$-C$_4$-alkyl, —C$_1$-C$_4$-alkoxy, halo(Cl, Br, F, I), —NO$_2$, —CO$_2$H, —CO$_2$—C$_1$-C$_4$-alkyl, —NH$_2$, —NH(-C$_1$-C$_4$-alkyl) and —N(C$_1$-C$_4$-alkyl)$_2$,
  (c) C$_3$-C$_4$-cycloalkyl,
  (d) C$_1$-C$_4$-alkyl which can be optionally substituted with a substituent that is a member selected from the group consisting of aryl as defined above, heteroaryl as defined above, —OH, —SH, —C$_1$-C$_4$-alkyl, —O(C$_1$-C$_4$-alkyl), —S(-C$_1$-C$_4$-alkyl), —CF$_3$, Halo(CL, Br, I, F), NO$_2$, —CO$_2$H, —CO$_2$—C$_1$-C$_4$-alkyl, —NH$_2$, —NH(-C$_1$-C$_4$-alkyl), —NHCOR$^{4a}$, —(C$_1$-C$_4$-alkyl)$_2$, PO$_3$H, —PO(OH)(C$_1$-C$_4$-alkyl) —PO(OH)aryl) or —PO(OH)(O—C$_1$-C$_4$-alkyl),
  (e) perfluoro-C$_1$-C$_4$-alkyl;
R$^{4a}$ is C$_1$-C$_6$-alkyl, aryl or —CH$_2$-aryl where aryl is as defined above; or the pharmaceutically acceptable salt thereof.

23. The process of claim 22 wherein
E is a single bond;
R$^6$ is —C$_2$-alkyl; and
—A—B—C—D— represents the constituent atoms of a 6-membered unsaturated heterocyclic ring with the imidazole to which they are attached containing 1 to 3 nitrogen atoms and includes the following:

$$\begin{array}{c} R^7 \quad R^7 \quad R^7 \\ | \quad\quad | \quad\quad | \\ -C=C-C=N-, \end{array}$$

$$\begin{array}{c} R^7 \quad R^7 \\ | \quad\quad | \\ -C=C-N=N-, \end{array}$$

$$\begin{array}{c} R^7 \quad R^7 \\ | \quad\quad | \\ -N=C-C=N-, \end{array}$$

$$\begin{array}{c} R^7 \quad\quad R^7 \\ | \quad\quad\quad | \\ -C=N-C=N-, \end{array}$$

$$\begin{array}{c} R^8 \quad O \quad R^8 \quad O \\ | \quad\quad \| \quad\quad | \quad\quad \| \\ -N-C-N-C-, \end{array}$$

$$\begin{array}{c} O \quad R^8 \quad R^8 \quad O \\ \| \quad\quad | \quad\quad | \quad\quad \| \\ -C-N-N-C-, \end{array}$$

$$\begin{array}{c} O \quad R^8 \\ \| \quad\quad | \\ -C-N-N=N-. \end{array}$$

24. The process of claim 11 wherein Q is W-L, where L is —(CH$_2$)—; and
W is $$\begin{array}{c} R^{1'}\diagdown\underset{N}{\overset{N}{\diagup\diagdown}}\underset{\underset{\downarrow}{}}{\overset{A}{\diagup\diagdown}}\overset{R^{3'}}{\underset{R^{4'}}{}} \end{array}$$

wherein
A, together with the adjacent vinylene group of the imidazole moiety completes an azene ring selected from pyridine, pyrimidine, pyridazine or pyrazine ring;
R$^{1'}$ is (1–8C)alkyl, (3–8)cycloalkyl, (3–8C)cycloalkyl-(1–4C)alkyl, phenyl or phenyl(1–4C)alkyl;
R$^{2'}$ is hydrogen, (1–4C)alkyl, (1–4C)alkoxy, halo(Cl, Br, F, I) trifluoromethyl, cyano or nitro;
R$^{3'}$ and R$^{4'}$ are optional substituents on the said azene ring, independently selected from hydrogen, (1–4-C)alkyl, (3–8C)cycloalkyl, (1–4C)alkoxy, halo(Cl, Br, F, I), trifluoromethyl, cyano, hydroxy, hydroxymethyl, formyl, and nitro; or
when A together with the imidazole moiety to which it is attached is an imidazo[4,5-b]pyridine or imidazo[4,5-c]pyridine group, R$^{3'}$ and R$^{4'}$ when they are on adjacent carbon atoms of A form a trimethylene or tetramethylene group, or together with the adjacent vinylene group of A complete a benzene ring, the later optionally bearing a halo(Cl, Br, I, F), (1–4C)alkyl or (1–4C)alkoxy substituent; or A together with the imidazole moiety to which it is attached is other than 1H-imidazo[4,5-c]pyridine ring, one of $R^{3'}$ or $R^{4'}$ is a carboxy or (1–6C)alkoxycarbonyl group and the other is as defined above; or a pharmaceutically acceptable salt thereof.

25. The process of claim 1 wherein W is a group of the following formula:

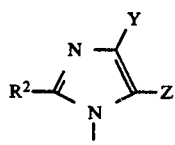

wherein $R^2$ is $C_1$–$C_4$ alkyl;

Y is $C_1$–$C_4$ alkyl, $C_1$–$C_4$ perfluoroalkyl, halogen, phenyl unsubstituted or substituted with one or two substituents selected from $C_1$–$C_4$ alkyl, F, Cl, $CF_3$, $C_1$–$C_4$ alkoxyl, alkoxyl, phenoxyl, phenyl; phenyl $C_1$–$C_4$ alkyl; and Z is hydroxymethyl, formyl, $C_1$–$C_4$ acyl, $C_1$–$C_4$ alkoxylcarbonyl, carboxyl, or Y and Z can be taken together to form a 5-, 6-, or 7-membered ring containing 1 to 2 heteroatoms selected from nitrogen, sulfur, or oxygen.

26. The process of claim 1 wherein W is a group of the following formula:

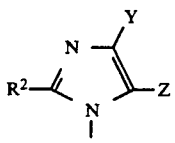

wherein $R^2$ is $C_1$–$C_4$ alkyl;

Y is $C_1$–$C_4$ alkyl, $C_1$–$C_4$ perfluoroalkyl, halogen, phenyl unsubstituted or substituted with one or two substituents selected from $C_1$–$C_4$ alkyl, F, Cl, $CF_3$, $C_1$–$C_4$ alkoxyl, alkoxyl, phenoxyl, phenyl; phenyl $C_1$–$C_4$ alkyl; and Z is hydroxymethyl, formyl, $C_1$–$C_4$ acyl, $C_1$–$C_4$ alkoxylcarbonyl, carboxyl.

27. The process of claim 26 wherein $R^2$ is $C_4$ alkyl,

Y is Cl, and

Z is hydroxymethyl.

28. A process for preparing 2-n-butyl-4-chloro-1-[(2'-(2-triphenylmethyl-2H-tetrazol-5-yl)-1,1'-biphenyl-4-yl)methyl]-1H-imidazole-5-methanol, the compound of Formula B

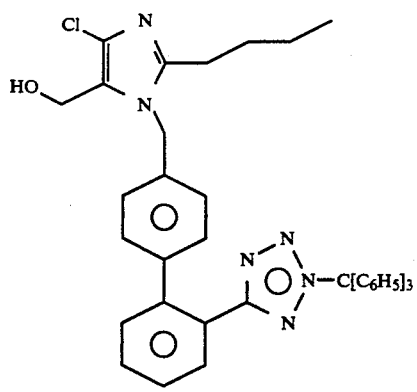

which comprises the following steps:
(a) mixing a compound of formula A

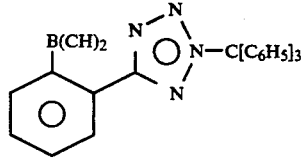

with coupling solvents, wherein the coupling solvents are water, tetrahydrofuran, and diethoxymethane, for 30 minutes;
(b) adding to the mixture a base, wherein the base is potassium carbonate, and a compound having the formula:

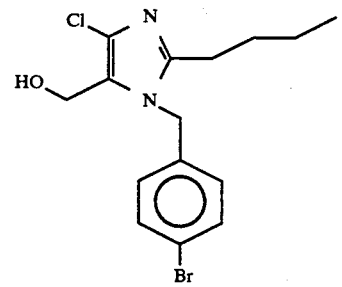

and mixing for 30 minutes;
(c) charging the mixture of step (b) with a metal catalyst, bis(triphenylphosphine)palladium acetate, which is generated in the reaction mixture by contacting palladium acetate and triphenylphosphine in tetrahydrofuran from room temperature up to 60° C. for 30 minutes, and heating to reflux at a temperature range of 76°–79° C. for 2–6 hours to produce the compound of formula B;
(d) purifying the reaction mixture containing the compound of formula B which comprises:
 (i) diluting the reaction mixture with tetrahydrofuran and water;
 (ii) isolating the organic solvent soluble layer containing the compound of formula B,
 iii) treating the organic solvent soluble layer containing the compound of formula B with tributylphosphine;
 (iv) distilling off the tetrahydrofuran from the organic solvent soluble layer containing the compound of formula B and tributylphosphine; and
 (v) diluting with diethoxymethane and distilling off the diethoxymethane to produce the residue of the compound of formula B.

29. The process of claim 28, which further comprises:
(a) crystallizing the compound of formula B from diethoxymethane and water to give the purified compound of formula B; and
(b) recrystallizing the purified compound of formula B of step (a) with a recrystallizing solvent, wherein the recrystallization solvent is methyl isobutyl ketone or a mixture of diethoxymethane and water, to produce the crystalline form of the compound of formula B.

* * * * *